(12) United States Patent
Peters et al.

(10) Patent No.: US 9,919,090 B2
(45) Date of Patent: Mar. 20, 2018

(54) BALANCING UNIT, EXTERNAL MEDICAL FUNCTIONAL UNIT, TREATMENT APPARATUS AND METHODS

(75) Inventors: Arne Peters, Bad Homburg (DE); Alexander Heide, Eppstein (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 644 days.

(21) Appl. No.: 13/515,566

(22) PCT Filed: Dec. 15, 2010

(86) PCT No.: PCT/EP2010/007647
§ 371 (c)(1),
(2), (4) Date: Jul. 11, 2012

(87) PCT Pub. No.: WO2011/082783
PCT Pub. Date: Jul. 14, 2011

(65) Prior Publication Data
US 2012/0267309 A1  Oct. 25, 2012

(30) Foreign Application Priority Data
Dec. 16, 2009  (DE) .................. 10 2009 058 681

(51) Int. Cl.
*A61M 1/00* (2006.01)
*A61M 1/16* (2006.01)
(Continued)

(52) U.S. Cl.
CPC ............ *A61M 1/16* (2013.01); *A61M 1/1015* (2014.02); *A61M 1/1639* (2014.02); *A61M 1/101* (2013.01);
(Continued)

(58) Field of Classification Search
None
See application file for complete search history.

(56) References Cited

U.S. PATENT DOCUMENTS

| 3,709,222 A | 1/1973 | De Vries |
| 4,105,016 A * | 8/1978 | Donovan, Jr. .................. 600/16 |

(Continued)

FOREIGN PATENT DOCUMENTS

| DE | 25 52 755 A1 | 8/1976 |
| DE | 33 28 744 A1 | 2/1985 |

(Continued)

OTHER PUBLICATIONS

PCT International Search Report from PCT/EP2010/007647, dated Apr. 28, 2011.

(Continued)

*Primary Examiner* — Krishnan S Menon
*Assistant Examiner* — Bradley R Spies
(74) *Attorney, Agent, or Firm* — Fish & Richardson P.C.

(57) ABSTRACT

A balancing unit for medical fluids includes at least one balancing chamber and at least one conveying unit for filling the balancing chamber, in which the conveying unit is a pressure controlled conveying unit and/or is designed and provided for being operated in at least one operating state as a constant-pressure source. An external medical functional unit, a treatment apparatus and methods are also described.

22 Claims, 4 Drawing Sheets

(51) Int. Cl.
  *A61M 1/10* (2006.01)
  *A61M 1/14* (2006.01)
  *A61M 1/28* (2006.01)

(52) U.S. Cl.
  CPC ......... *A61M 1/1001* (2014.02); *A61M 1/1006* (2014.02); *A61M 1/1031* (2014.02); *A61M 1/1086* (2013.01); *A61M 2205/12* (2013.01)

(56) References Cited

U.S. PATENT DOCUMENTS

| | | | |
|---|---|---|---|
| 4,997,570 A | | 3/1991 | Polaschegg |
| 5,326,476 A | * | 7/1994 | Grogan ................... A61M 1/16 210/321.65 |
| 5,542,919 A | | 8/1996 | Simon et al. |
| 5,725,357 A | | 3/1998 | Nakazeki et al. |
| 6,171,078 B1 | * | 1/2001 | Schob ........................ 417/423.1 |
| 2005/0048461 A1 | | 3/2005 | Lahteenmaki |
| 2005/0131332 A1 | | 6/2005 | Kelly et al. |
| 2009/0095679 A1 | | 4/2009 | Demers et al. |

FOREIGN PATENT DOCUMENTS

| | | |
|---|---|---|
| DE | 101 00 146 A1 | 7/2002 |
| EP | 0 623 357 A1 | 11/1994 |
| EP | 0623357 A1 | 11/1994 |
| EP | 0 867 195 B1 | 9/1998 |
| EP | 0 900 572 A1 | 3/1999 |
| JP | S52-139298 | 11/1977 |
| JP | H02-243161 | 9/1990 |
| JP | H08-164201 | 6/1996 |
| JP | 08-270595 H | 10/1996 |
| JP | 2008055185 A | 3/2008 |
| JP | H05-031179 | 9/2012 |

OTHER PUBLICATIONS

Japanese Search Report by Registered Searching Organization in Japan Application No. 2012- 543521, dated Sep. 11, 2014, 34 pages. (with English translation).

* cited by examiner

US 9,919,090 B2

BALANCING UNIT, EXTERNAL MEDICAL FUNCTIONAL UNIT, TREATMENT APPARATUS AND METHODS

CROSS-REFERENCE TO RELATED APPLICATIONS

The present application is the national stage entry of International Patent Application No. PCT/EP2010/007647, filed on Dec. 15, 2010, and claims priority to Application No. DE 10 2009 058 681.4, filed in the Federal Republic of Germany on Dec. 16, 2009.

FIELD OF INVENTION

The present invention relates to a balancing unit. It further relates to an external medical functional unit, and a treatment apparatus as well as methods.

BACKGROUND INFORMATION

European Patent No. EP 0 867 195 B1 describes balancing units for balancing mass and/or volume flows of medical fluids, such as blood or fluids used during the blood treatment.

SUMMARY

One object of the present invention is to propose a further balancing unit.

This object may be solved by a balancing unit for balancing medical fluids, in particular for balancing dialysate.

The balancing unit according to the present invention may comprise at least one balancing chamber and at least one conveying unit for filling the balancing chamber.

According to the present invention, the conveying unit may be a pressure controlled conveying unit or pressure limited conveying unit.

In all of the following embodiments, the use of the term "can be" or "can have" or "can comprise," respectively, etc. is to be understood as a synonym for "preferably is" or "preferably has" or "preferably comprises," respectively, etc.

The term "balancing" or "balancing process," respectively, as used herein is, in one embodiment, to be understood as a comparison of masses and/or volumes of medical fluids supplied to or drawn from a patient or a treatment apparatus for treating the patient.

The term "patient" as used herein refers to a human or an animal, independently from being ill or healthy.

In the sense of the present invention, a "balancing chamber" refers to a unit or device, respectively, provided or intended to receive the medical fluids—or portions thereof—intended for balancing in an interior or inner volume, respectively.

In one embodiment according to the present invention, the balancing chamber is a chamber that is separated in at least two balancing chamber compartments or sections by means of at least one separating plate or membrane that can be designed displaceable or flexible. At least one of the balancing chamber compartments or sections can be provided or intended to receive supplied or fresh, respectively, medical fluids. At least one further balancing chamber compartment or one further balancing chamber section can be provided or intended to receive discharged or used, respectively, medical fluids.

The balancing unit can comprise more than one balancing chamber, i.e., e.g., two, three, four or more balancing chambers.

Several, e.g., two, balancing chambers can, for example, advantageously be used for ensuring a continuous flow of the medical fluids during the balancing process.

The balancing chambers can be in fluid communication or not. The balancing chambers can be fillable and/or dischargeable in common or separately.

Each balancing chamber can comprise (one or more) supply lines for supplied or fresh medical fluids and (one or more) drain lines connected with an outlet for discharged or used medical fluids. Shut-off valves may be arranged in the supply and/or drain lines.

Examples of such shut-off valves include actuators that can be retracted from and/or pushed into a part of a machine, such as a treatment apparatus. By means of these actuators, it can be possible to prevent or release a fluid flow within a fluid system of the medical fluids. Such actuators include actuators referred to as "phantom valves" as described in Application No. DE 10 2009 024 468.9, filed by the applicant of the present application in the Federal Republic of Germany on Jun. 10, 2009 and having the title "Externe Funktionseinrichtung, Blutbehandlungsvorrichtung zum Aufnehmen einer erfindungsgemäßen externen Funktionseinrichtung, sowie Verfahren," which is expressly incorporated herein in its entirety by reference thereto.

Examples of balancing chambers according to one embodiment of the balancing unit of the present invention as well as their respective function are disclosed in the aforementioned European Patent No. EP 0 867 195 B1, filed by the applicant of the present invention and which is expressly incorporated herein in its entirety by reference thereto.

The conveying unit can be part of a fluid system in which the medical fluid is present or contained, respectively. The conveying unit can be built-in or switched into, respectively, the fluid system, e.g., for conveying the medical fluid. In or during its use, the conveying unit can be flowed through by the medical fluid to be balanced.

The fluid system can comprise lines, tubings, tubing systems, channels, chambers, indentations, units or devices, respectively, or spaces or areas for storing or retaining fluids as well as controlling devices for controlling or regulating a through-flow of the fluids, and the like.

In certain embodiments, the fluid system is provided for a dialyzing liquid.

In certain embodiments, the fluid system is provided for blood in an extracorporeal blood circuit or other fluids. Such other fluids comprise a citrate and/or calcium solution, water or a hydraulic liquid.

The pressure present in the balancing chamber upon filling is in the following referred to as filling pressure. It can be changeable. It can be increasing. It can have different values at different points of time.

In one embodiment, a maximum filling pressure of the balancing unit according to the present invention can be set by means of an adjusted rotation speed of the conveying unit. The maximum filling pressure can be predetermined by means of the characteristic curve of the conveying unit, e.g., a characteristic curve of a pump.

In one embodiment, the flow and/or the conveying pressure of the conveying unit is measured by using appropriate measuring units. Corresponding measuring units may be configured and provided therefor.

The maximum filling pressure for filling the balancing chamber of the balancing unit can be predetermined. In one embodiment according to the present invention, the maximum filling pressure can be set or is set, respectively, by changing the operating parameters of the conveying unit (e.g., by influencing the rotation speed of a pump).

In a further embodiment according to the present invention, the operating parameters of the conveying unit can be set or are set, respectively, (e.g., by influencing the rotation speed of a pump) by changing a magnetic field.

In one embodiment, the maximum filling pressure—after having been reached—can be maintained constant by the conveying unit for a certain time or can, in another embodiment, drop. This can happen depending on the preload.

The maximum filling pressure can, for example, be reached when the balancing chamber is substantially or completely filled by the one or more medical fluids to be balanced.

The maximum filling pressure can also be reached when a balancing chamber compartment or a balancing chamber section has been substantially or completely filled by operating the conveying unit.

In one embodiment of the balancing unit according to the present invention, the "pressure controlled conveying unit" or the "pressure limited conveying unit," respectively, is a conveying unit that does not build up any higher pressure within the balancing chamber after having reached a maximum pressure or filling pressure.

In another embodiment of the balancing unit according to the present invention, the "pressure controlled conveying unit" or the "pressure limited conveying unit" is a pump, the impeller of which is overflowed by the fluid conveyed upon reaching the maximum filling pressure.

In a further embodiment of the balancing unit according to the present invention, the "pressure controlled conveying unit" is a conveying unit which can, in at least one operating state, be operated as a constant-pressure source or as a pressure source having a constant or approximately constant pressure.

In a further embodiment of the balancing unit according to the present invention, the "pressure controlled conveying unit" is a conveying unit comprising or consisting of at least one pump, wherein the pump does not comprise or is not functionally connected with any overflow valves and/or bypass lines.

In a further embodiment of the balancing unit according to the present invention, the "pressure controlled conveying unit" is a conveying unit which is not connected with a control unit for the purpose of controlling or limiting, respectively, the pressure of the conveying unit depending on the filling pressure present in a balancing chamber during filling the said balancing chamber and/or which does not comprise a control unit that is provided or intended for this purpose and configured correspondingly.

In a further embodiment of the balancing unit according to the present invention, the "pressure controlled conveying unit" is a pump that—due to its design or construction, respectively,—does not build up a pressure above a predetermined pressure—here the filling pressure. In at least one embodiment of the balancing unit according to the present invention, it is herein not—directly or indirectly, respectively,—assisted or supported, respectively, by any further elements or components, in particular no control unit, no switching mechanism, no valves, no bypass gauge pressure valves, no pressure measuring units, and the like.

If the balancing chamber filled by the conveying unit can be assumed to be a volume-fixed chamber after having reached a maximum pressure or filling pressure set by means of the machine, the conveying unit is called a "pressure controlled conveying unit" as is the case in one embodiment according to the present invention.

In one embodiment according to the present invention, the balancing unit comprises several conveying units.

In one embodiment according to the present invention, the balancing unit does not comprise any overflow valves, bypass lines, control units, switching mechanisms, valves, bypass gauge pressure valves, pressure measuring units, and the like, that are suited and provided or intended or configured for limiting the conveying pressure of the conveying unit.

In one embodiment according to the present invention, the balancing unit does not comprise a roller pump or a gear pump comprising a bypass valve and/or a pressure regulation.

If the balancing unit according to the present invention comprises several conveying units, the said conveying units could, in one embodiment, be designed in the same manner or differently.

In one embodiment according to the present invention of the balancing unit, the said balancing unit comprises several conveying units connected in series. In this way, it can advantageously be possible to disburden or unload, respectively, the balancing chamber in a controlled manner.

In one embodiment according to the present invention of the balancing unit, the single conveying units are arranged for running or being operated, respectively, in the same direction of conveyance or for conveying in the same direction, respectively.

In one embodiment according to the present invention, the conveying units run in different directions or convey in opposite directions, respectively. Hereby, it can advantageously be possible to build up pressure in a targeted manner and/or to limit the volume flow of the medical fluids. This can advantageously contribute to further reducing the forces acting on the balancing chamber. In particular, it can advantageously be possible to reduce or to even minimize the forces acting on the balancing chamber and the walls thereof.

In one embodiment according to the present invention, at least two conveying units run or convey, respectively, in the same direction. Hereby, it can advantageously be possible to reduce pressure in a targeted manner. This may also advantageously contribute to further reducing the forces acting on the balancing chamber (unloading the chamber). In particular, it can advantageously be possible to reduce or to even minimize the forces acting on the balancing chamber and the walls thereof.

In a further embodiment of the balancing unit according to the present invention, the "pressure controlled conveying unit" is a centrifugal pump, a pressure source, a membrane pump or a rotary pump.

In one embodiment, a "centrifugal pump" or a rotary pump can advantageously provide a high volume flow at low pressures and/or a low volume flow at high pressures.

In one embodiment according to the present invention, the centrifugal pump is an axial pump having the advantages known to a person skilled in the art in connection with axial pumps.

In a further embodiment according to the present invention, the centrifugal pump is a radial pump or a diagonal pump having the advantages known to a person skilled in the art in connection with radial pumps or diagonal pumps, respectively.

The maximum pressure of the centrifugal pump—and thus the maximum filling pressure—can be set by the rotation speed, e.g., by means of rotation speed control, such that the maximum pressure load on the entire system can advantageously be defined (highly) exactly.

The centrifugal pump can have the characteristic that an overflow of the impeller or of the rotational section, respectively, occurs above a certain fluid pressure, e.g., when the balancing chamber is completely filled. This overflow can result in a pressure control in the fluid conveyed such that the centrifugal pump operates in a pressure controlled manner in the sense of the present invention.

For achieving the pressure control the centrifugal pump does, in one embodiment, advantageously not require any assistance by further components, such as a control unit, a regulation unit, valves, etc.

According to the present invention, a pressure source is understood to be any fluid conveying apparatus the initial fluid pressure of which is constant or substantially constant.

By means of the incompressible pumped liquid or a corresponding fluid, the membrane pump generates exactly the pressure in the liquid or the fluid with which the membrane is operated or actuated, respectively (e.g., mechanically, electromagnetically, pneumatically or hydraulically). Thus, in a further embodiment of the present invention, a membrane pump is to be considered as a pressure source, in particular as a pressure controlled conveying unit.

In a further preferred embodiment, the conveying unit comprises at least one rotating section or rotational section, respectively. In one embodiment according to the present invention, the latter is supported by a mechanical bearing; in another embodiment, it is supported by a magnetic bearing.

The rotational section can exclusively or additionally be supported magnetically.

The rotational section can be arranged in an interior of the conveying unit.

In or during its use, the rotational section can be completely flushed by the medical fluids flowing through the conveying unit.

In one embodiment, the rotational section is an impeller or a rotor.

In a further embodiment, the conveying unit comprises at least one rotational section intended and designed for being actuated or operated magnetically by means of an external actuation or by means of an electrical field.

In a further embodiment, the external actuation of the rotational section is designed to be operated mechanically, e.g., by means of releasable fluid-tight couplings.

The term "external actuation" as used herein refers to an actuation for the rotational section that can be but does not have to be part of the balancing unit.

The external actuation can be arranged at an apparatus interacting with a balancing unit according to the present invention, such as a treatment apparatus. The external actuation can be part of the apparatus.

The magnetic driving or propelling, respectively, force or effect can by achieved by using one or more magnets. It can be achieved by using current-carrying conductors or live conductors, respectively. For example, live coils can be used.

In one embodiment according to the present invention of the balancing unit, the conveying unit is a magnetically supported centrifugal pump such as, for example, that described in European Patent Application No. EP 0 900 572 A1.

Such a magnetically supported centrifugal pump can—like every other magnetically supported conveying unit in the sense of the present invention—offer the advantage that a mechanical and/or electrical interface to the machine is not required and/or fluids do not have to be transferred from the machine or the treatment apparatus, respectively, to the pump.

In a further preferred embodiment, the medical fluid is selected from dialyzing liquid, blood, substitute liquid, drugs, drug preparations as well as mixtures or combinations thereof.

In one embodiment according to the present invention, in particular, balancing on the dialysate side during a dialysis is envisaged.

In one embodiment according to the present invention, balancing on the blood side during a dialysis is envisaged.

Further fluids that may be of interest and/or required for a balancing process in connection with a blood treatment of a patient include solutions or metabolites of the patient present in a solved form, such as, for example, substances obligatory excreted by urine, and the like.

In a further preferred embodiment, at least one first conveying unit is provided for conveying in a first direction. Further, there is provided at least one second conveying unit for conveying in a second direction opposite to the first direction.

The object of the present invention is further solved by an external medical functional unit. All advantages achievable by means of the balancing unit according to the present invention can in certain embodiments undiminishedly also be obtained by means of the external medical functional unit according to the present invention that comprises at least one balancing unit according to the present invention.

In one embodiment of the present invention, the external medical functional unit is embodied or designed as an external liquid circuit having a dialysate and an extracorporeal blood circuit or as a blood or dialysate cassette, respectively, or as a combined blood/dialysate cassette. The external medical functional unit may, e.g., be a blood or dialysate cassette, respectively, or a combined blood/dialysate cassette for dialysis.

In one embodiment according to the present invention, the external medical functional unit is a disposable unit, a single use article or a one-use product.

In one embodiment according to the present invention, the external medical functional unit is a disposable cassette.

The disposable cassette can be a solid or hard part. It can be made from a plastic material. The disposable cassette can be manufactured by using an injection molding method.

The object of the present invention is further solved by means of a treatment apparatus. All advantages achievable by means of the balancing unit according to the present invention can in certain embodiments undiminishedly also be obtained by means of the treatment apparatus according to the present invention.

The treatment apparatus according to the present invention is suited for treating medical fluids. It is designed to operate at least one balancing unit according to the present invention.

At least for this purpose, the treatment apparatus can comprise a control unit. The control unit can be or comprise a microprocessor.

In one preferred embodiment of the treatment apparatus according to the present invention, the treatment apparatus comprises a unit or device, respectively, provided or intended and configured for actuating the conveying unit of the balancing unit via a magnetic actuation interface.

The device or unit can, for example, be or comprise a magnet or a magnetic system and/or a live conductor such as, for example, one or more live coils.

The treatment apparatus can be connected functionally with a balancing unit according to the present invention and/or with an external medical functional unit according to the present invention.

In one embodiment according to the present invention, the treatment apparatus according to the present invention comprises at least one balancing unit according to the present invention.

In one embodiment according to the present invention, the treatment apparatus according to the present invention is firmly connected with the balancing unit according to the present invention.

In one embodiment according to the present invention, a repeated use of the firmly connected balancing unit according to the present invention is envisaged.

In one embodiment according to the present invention, the treatment apparatus according to the present invention is a hemodialysis device.

In certain embodiments, the treatment apparatus furthermore comprises further devices or units or is intended to be coupled therewith. Among those are, for example, an extracorporeal blood circuit, control devices for controlling the performance of a medical treatment, devices for monitoring and/or displaying a balancing process of the medical fluids used and/or circulated during a medical treatment, devices for displaying or representing states and/or parameters of the medical treatment or of the balancing process, such as screens, and the like, devices for operating or actuating, respectively, or controlling one or more components of the treatment apparatus, such as keypads, and the like, in order to, e.g., prompt the performance of a medical treatment, and the like.

In one embodiment according to the present invention, the treatment apparatus is a blood treatment apparatus.

Examples of blood treatment methods include dialysis methods such as a hemodialysis, in particular by using ultrafiltration, a hemodiafiltration, a peritoneal dialysis, an automatic peritoneal dialysis, and the like. For performing those methods, the blood treatment device can be designed or embodied correspondingly.

Finally, the balancing unit according to the present invention can be advantageously used in a peritoneal dialysis for determining the volume of the dialysis liquid that is directed into the peritoneal space of the patient and/or conveyed out of the patient therefrom. Thereby, for example, both balancing chamber compartments of a divided or bifid balancing chamber of the balancing unit can mutually be filled with fresh dialysis liquid (upon entrance of the dialysis liquid into the patient's abdomen) and/or with used dialysis liquid (upon removal of the dialysis liquid out of the patient's abdomen). The volumes and/or masses of the medical fluids, e.g., of the dialysis liquid, that are of interest during a balancing process can thereby, for example, be determined by the number of fillings of the balancing chamber.

The object of the present invention is further solved by a method. All advantages achievable by means of the balancing unit according to the present invention can undiminishedly also be obtained by the methods according to the present invention.

A method according to the present invention comprises balancing at least one medical fluid by using at least one balancing unit according to the present invention or at least one external medical functional unit according to the present invention or at least one treatment apparatus according to the present invention.

A method according to the present invention comprises filling a balancing chamber by means of at least one conveying unit and operating the conveying unit in at least one operating state as a constant-pressure source.

In order to operate the conveying unit in the desired operating state as a constant-pressure source, a certain rotation speed of the conveying unit can be set at which a fixed or definite, respectively, or predetermined pressure difference can be set in the conveying unit.

The present invention proposes a balancing unit in which the conveying unit can be operated as a constant-pressure source after filling the balancing chamber(s).

The constant-pressure source can advantageously contribute to ensuring a maximum filling pressure within the balancing chamber. The constructional requirements for the balancing chamber can thus be low.

Generally, the accuracy of a balancing process can primarily depend on the pressure variations between two filling procedures. This may result from the fact that the switching process for terminating a filling process is subject to minor variations and that the filling pressure or the pressure inside the chamber significantly increases at the end of the filling process.

Furthermore, it is known that a balancing chamber is usually not stable towards pressure. For this reason, its filling volume can change.

As the medical fluids introduced into the balancing chamber by means of the conveying unit can displace the fluids present in the balancing chamber to the same degree or with the same speed or rate, respectively, it can advantageously be possible to reach a constant or uniform mass and/or volume flow of the fluids to be balanced.

As a pressure difference for operating the balancing chamber can be set in an advantageously simple manner by means of the rotation speed and/or the maximum conveying pressure of the conveying unit, the pressure controlled conveying unit can set an advantageously precisely adjustable (also dynamically adjustable) balancing chamber pressure while balancing the medical fluids.

An adverse pressure increase and/or pressure variations of the balancing chamber can thus advantageously be prevented. An undesired volume expansion or change of the balancing chamber can thus advantageously be prevented.

In this way, it can advantageously be possible to improve a mass and/or volume accuracy of a balancing process.

This can, for example, also advantageously contribute to exactly determining the fluid volume that is drawn from a patient during a treatment, e.g., ultrafiltration during a dialysis treatment, via the dialysis filter membrane, and/or to set the said fluid volume onto the rate desired by the attending physician. The safety and optionally also the tolerance of a blood treatment can thus advantageously be further improved.

Thus, it can advantageously be possible to prevent an incorrect balancing wherein an incorrect balancing can add up, e.g., in the course of a blood treatment session. If the balancing influences the treatment performed, the balancing accuracy improved by means of the balancing unit according to the present invention in at least one embodiment can advantageously result in an improved and/or safer treatment, e.g., by setting the ultrafiltration rate in a more adequate manner.

The balancing chamber of the balancing unit according to the present invention can advantageously be used as a pressure controlled volumetric balancing chamber having sufficient stability.

Technically complex constructions such as strut members or reinforced plastic materials or the like, with which a sufficient stability has to be ensured in the state of the art, can advantageously be omitted when using the balancing unit according to the present invention. The construction of the balancing unit according to the present invention can thus advantageously be simplified due to the pressure control provided by means of the conveying unit.

Supporting walls of the balancing chamber at fixed structures of the treatment apparatus is not required. The usability of the balancing unit has thus become broader without losing its functional accuracy.

Additionally, the conveying unit in the balancing unit according to the present invention can advantageously do without using sensors and/or overflow valves and/or bypass gauge pressure valves, in particular for the purpose of limiting the pressure in an interior of the balancing chamber, and the like. Thus, it can further advantageously be possible to simplify operating the balancing unit. The conveying unit may be designed more simply.

In this way, the dimensions of the balancing unit or the required space for the balancing unit, respectively, can advantageously be kept small.

Due to the magnetic support of the conveying unit, the construction of the conveying unit can advantageously be simplified. Thus, it can advantageously be possible to omit mechanical components such as bearings and the like and to thus advantageously ensure little wear of the components and/or little abrasive wear. This advantageously allows avoiding or reducing a heating of the conveying unit or of the balancing unit.

Moreover, the conveying unit of the balancing unit according to the present invention can advantageously comprise little disposition for cavitation.

Another advantage can be only little noise development upon using the balancing unit according to the present invention.

Because the pressure of the conveying unit does not increase even with an ongoing volume flow after terminating the filling of the balancing chamber, it can advantageously be avoided having to shut down the conveying unit in case of a full, i.e. substantially or completely filled, balancing chamber. Thus, a fluid, e.g., flowing through the centrifugal pump, can overflow a rotational section of the centrifugal pump. In this way, a good rinseability (and flushability) of the conveying unit can be ensured with a directed flow within the space of the centrifugal pump in which fluid flows.

The magnetic actuation interface for operating the conveying unit or a rotational section thereof, respectively, can advantageously provide a contactless and/or seal-free actuation of the conveying unit. In this way, it can advantageously be possible to omit open interfaces between the balancing unit and the treatment apparatus.

It can thus advantageously be possible to ensure a particular safe operation of the balancing unit. An—albeit only extremely small—contamination risk of the medical fluids can thus advantageously be reduced and even completely excluded.

The balancing unit according to the present invention can advantageously be used as a disposable unit, i.e. as a one-way article for single use. As the conveying unit can be provided as an integral component of the disposable unit, it can be discarded together with the disposable unit such that the safety and the hygiene of a medical treatment can advantageously be further improved.

The use of centrifugal pumps has in certain embodiments the advantage of an inherent pressure control in case of an occlusion downstream the pump as compared to pressure-regulated peristaltic hose pumps, toothed gear pumps or peristaltic pumps. The pressure built up there can be adjusted by the rotation speed in a simple manner. A pressure-regulated peristaltic hose pump requires at least one pressure sensor comprising a control circuit; a peristaltic hose pump comprising a gauge pressure bypass valve has to be exactly calibrated to the allowed pressure. Thus, by using centrifugal pumps, the balancing unit according to the present invention is in certain embodiments less complex.

Exemplary embodiments of the present invention will be described with respect to the accompanying drawings. In the drawings, the same reference numerals denote same or identical elements or components, respectively.

DETAILED DESCRIPTION

In the following, the balancing unit is exemplarily described as a part of a blood treatment apparatus for dialysis. It is intended to balance the dialysis liquid supplied to and drawn from a patient. However, it can in principle also be envisaged to balance the patient's blood.

Figure 1:
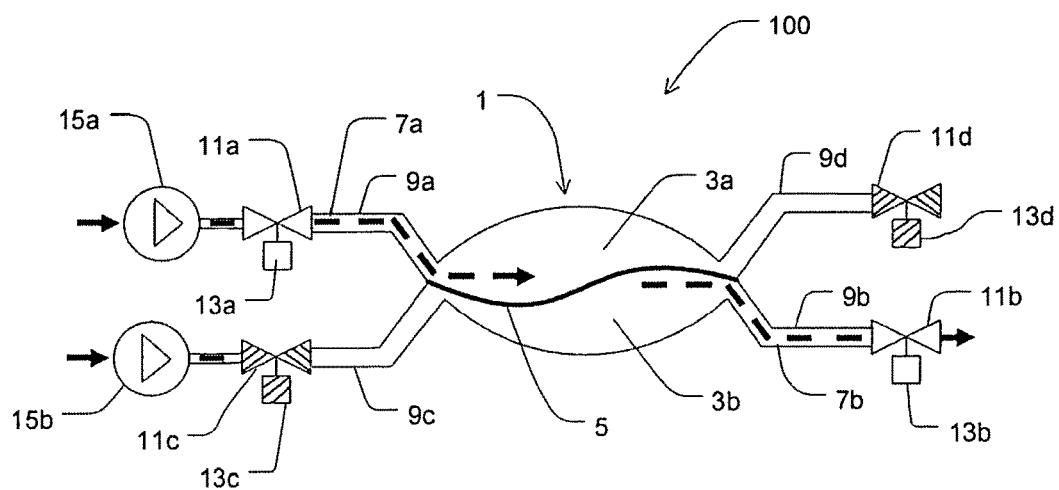
FIG. 1 shows an exemplary balancing unit according to the present invention during a first cycle in a schematically simplified manner.

FIG. 1 shows an exemplary balancing unit 100 according to the present invention comprising a balancing chamber 1.

As shown in FIG. 1, the balancing chamber 1 is separated or divided into a first balancing chamber compartment 3a and into a second balancing chamber compartment 3b. However, the balancing chamber does in principle not have to be divided in two balancing chamber compartments having substantially or completely the same size.

The first balancing chamber compartment 3a is separated from the second balancing chamber compartment 3b by means of a fluid-tight membrane 5.

The first balancing chamber compartment 3a is filled with a flow 7a of a dialysis liquid via a tubing 9a. A valve 11a is thereby present in an opened position by means of a controlling unit 13a.

The conveying unit can be a centrifugal pump. As shown in FIG. 1, the first chamber compartment 3a is filled by means of a centrifugal pump 15a.

The valve 11a can be designed as a tubing clamp (or generally as a squeezing mechanism). Such a tubing clamp can be opened and closed by means of an electrically controlled actuation. This has the advantage that the medical fluid substantially only contacts the tubing 9a, but, however, does not contact parts of the valve 11a or of the controlling unit 13a. This can advantageously contribute to reducing a contamination risk of the medical fluids.

A second flow 7b of the dialysis liquid is discharged out of the second balancing chamber compartment 3b via a tubing 9b. A valve 11b is thereby also present in an opened position, mediated by means of a controlling unit 13b.

The second balancing chamber compartment 3b can be emptied. Discharging or draining dialysis liquid out of the second balancing chamber compartment 3b can be effected at the same time as supplying or introducing dialysis liquid into the first balancing chamber compartment 3a.

As shown in FIG. 1, valves 11c and 11d are each closed by means of the corresponding controlling units 13c and 13d. There is no fluid conveyed in tubings 9c and 9d.

Figure 2:
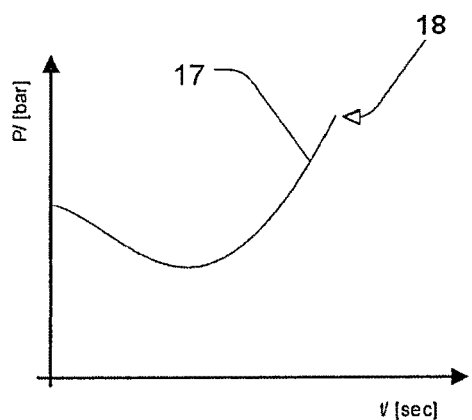
FIG. 2 shows an exemplary pressure curve plotted against the time during filling a balancing chamber.

FIG. 2 shows a diagram representing an exemplary pressure curve or course 17 during filling a balancing chamber plotted against the time.

An initial pressure at t=0 corresponds to a pressure with which in FIG. 1—which is in the following also referred to—the flow 7a of the dialysis liquid is introduced into the first balancing chamber compartment 3a via the tubing 9a after opening the valve 11a. In order to allow discharging flow 7b of the dialysis liquid via tubing 9b out of the second balancing chamber compartment 3b, valve 11b should be opened.

While the first balancing chamber compartment 3a is filled and the second balancing chamber compartment 3b is emptied, the pressure in the balancing chamber drops at first.

When the first balancing chamber compartment 3a has been filled, the pressure rises. A final pressure 18 corresponding to the end point of the pressure course 17 during filling of the balancing chamber and thus corresponding to the maximum filling pressure can depend on the pressure applied by the centrifugal pump 15a. This pressure can in turn depend on several parameters of the centrifugal pump, for example, on the construction principle of the centrifugal pump (radial pump, axial pump, diagonal pump, impeller shape, impeller diameter, etc.) and/or the set rotation speed of the centrifugal pump 15a and thus the set operating point. Moreover, the final pressure can depend on the preload of the centrifugal pump 15a, i.e., the pressure present at a dialysate inlet of the centrifugal pump 15a.

Figure 3:
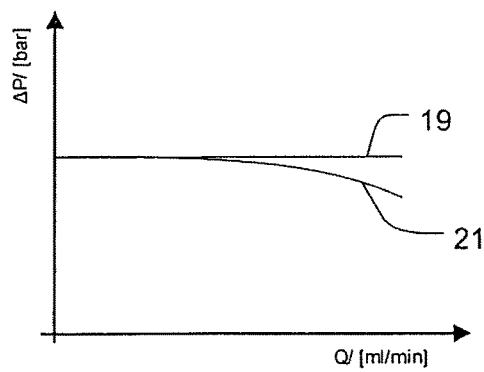
FIG. 3 shows an exemplary pressure difference between the pump outlet and the pump inlet of a centrifugal pump plotted against the volume flow.

FIG. 3 shows a diagram comprising an exemplary pressure difference ΔP between the pump outlet and the pump inlet of a centrifugal pump 15a (ordinate) plotted against the volume flow Q of the medical fluids (abscissa).

At a characteristic curve 19 of an ideal pressure source which is indicated for comparison, the pressure difference ΔP is independent from the volume flow Q. The amount or extent, respectively, of the pressure difference ΔP depends, inter alia, on the set rotation speed of a centrifugal pump.

The actual pressure courses (ΔP, Q) usually divert from the ideal characteristic curve. A possible pressure course of a characteristic curve for a pressure controlled conveying unit such as the centrifugal pump 15a of the balancing unit 100 according to the present invention of FIG. 1 is shown by characteristic curve 21 of a centrifugal pump. It can be recognized that a good approximation of the pressure course to the ideal characteristic curve can be obtained by means of the centrifugal pump 15a. FIG. 3 also shows that the centrifugal pump 15a can be understood as a pressure controlled conveying unit in the sense of the present invention: Despite an increase of a volume flow, the pump outlet pressure does not increase anymore after having reached a certain pressure level.

Figure 4:
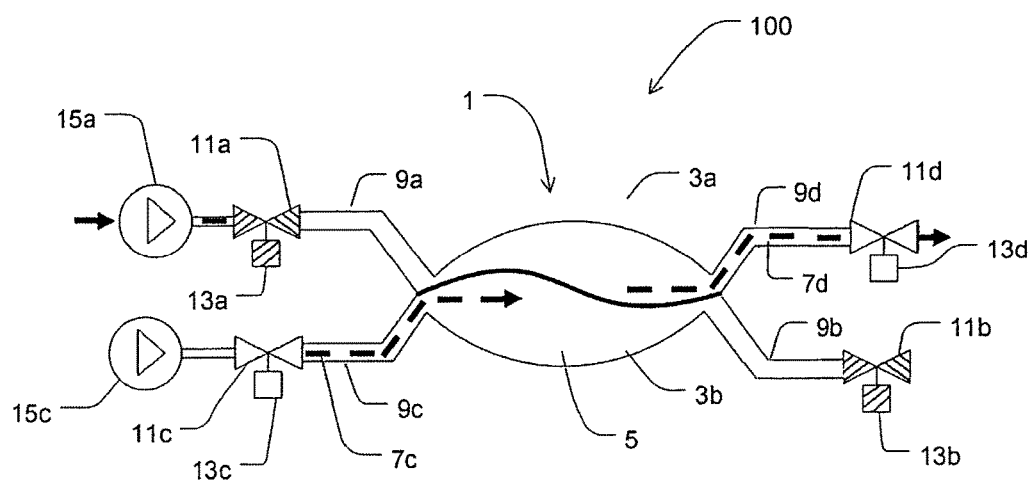
FIG. 4 shows the exemplary balancing unit according to the present invention of FIG. 1 during a second cycle in a schematically simplified manner.

FIG. 4 shows the exemplary balancing unit 100 of FIG. 1 during a second cycle. The second cycle can follow the first cycle according to FIG. 1.

In the second cycle of a centrifugal pump 15c, a flow 7c of dialysis liquid is conveyed into the second chamber compartment 3b via the tubing 9c. At the same time, a flow 7d of dialysis liquid is removed from the first chamber compartment 3a.

Figure 5:
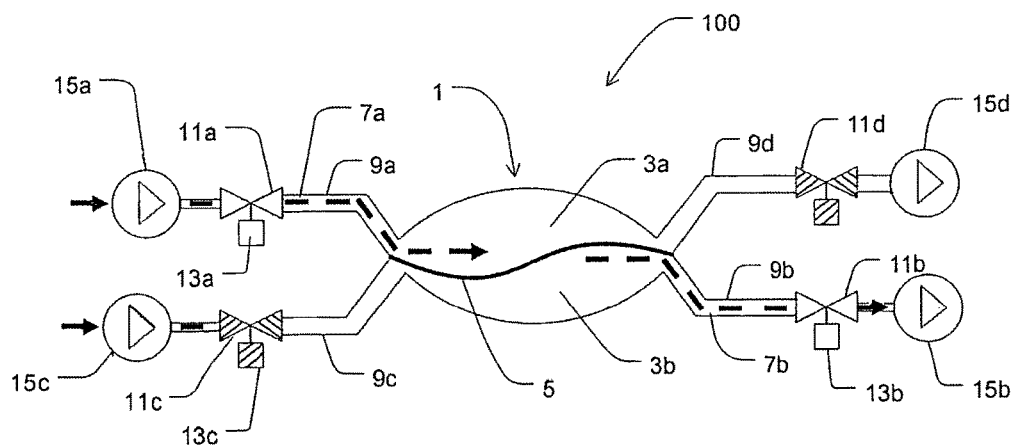
FIG. 5 shows the exemplary balancing unit according to the present invention of FIG. 1, comprising two further centrifugal pumps downstream the balancing chamber in a schematically simplified manner.

FIG. 5 shows the exemplary balancing unit 100 of FIG. 1 comprising two additional centrifugal pumps 15b and 15d downstream the balancing chamber 1.

All centrifugal pumps 15a-d arranged in the balancing unit 100 according to the present invention of FIG. 5 convey in the same direction of conveyance as indicated by the arrow of the pump heads pointing to the left (related to the representation of FIG. 5).

By means of the centrifugal pumps 15b and 15d arranged downstream, emptying the two chamber compartments 3a and 3b can be supported. This can be advantageous in order to, for example, reduce or keep low a maximum pressure (see end point 18 of the curve of the pressure course in FIG. 2) in the balancing chamber 1. Low pressures in the balancing chamber 1 can in turn advantageously contribute to simplifying the construction (such as, e.g., a lower stiffness, lower material thicknesses, etc.) of the balancing unit 100 as stated above. The latter could in particular be advantageous if the balancing unit 100 is embodied as a part of a disposable unit.

Figure 6:
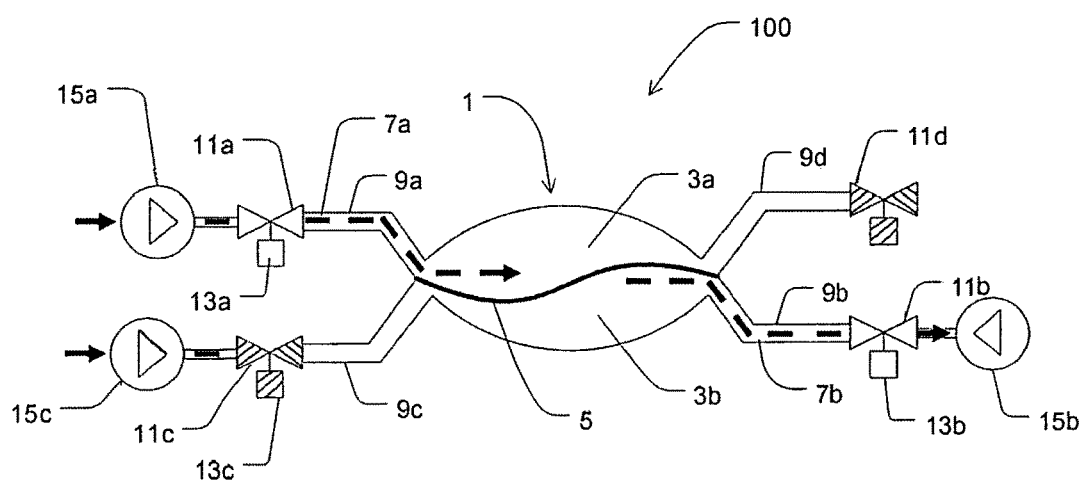
FIG. 6 shows the exemplary balancing unit according to the present invention comprising the balancing chamber, valves, and centrifugal pumps in a schematically simplified manner, wherein one of the centrifugal pumps arranged downstream rotates in another direction.

FIG. 6 shows the exemplary balancing unit 100 comprising the balancing chamber 1 similarly to FIG. 5, however, with the difference that the centrifugal pump 15b is provided or intended and configured for also running in another direction or conveying in the opposite direction, respectively, as indicated by means of the arrow of the pump head pointing to the left (related to the representation of FIG. 6).

When running in the opposite direction of rotation, the centrifugal pump 15b operates as a pressure reducer, in particular as an adjustable pressure reducer.

In the embodiment of FIG. 6, inlet and outlet of the centrifugal pump 15b can be interchanged.

"Interchanging" inlet and outlet can be effected in different ways. Examples hereof are reversely inserting the centrifugal pump, providing valves correspondingly arranged and controlled, and the like.

Valves correspondingly arranged and controlled can be preferably operated by means of actuators of a dialysis machine across a flexible membrane, e.g., by squeezing and/or releasing the relevant fluid paths.

A reversion of the direction can be intended additionally or alternatively. The conveying units contemplated can be provided or intended and configured to be operated in one direction or in two directions opposite to each other.

Figure 7:
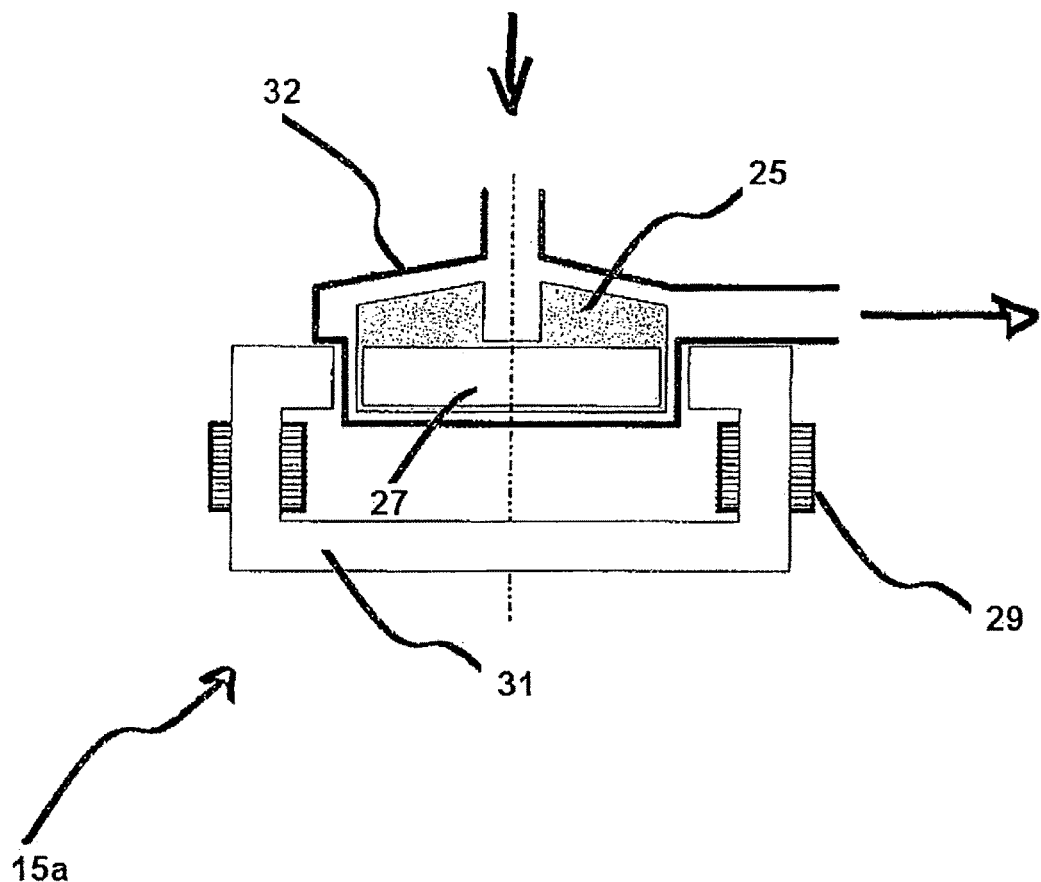
FIG. 7 shows an exemplary centrifugal pump comprising a magnetic support and a magnetic actuation in a schematically simplified manner.

FIG. 7 shows an exemplary centrifugal pump 15a comprising an impeller 25 as a rotational section, a rotor 27, coils 29 and a stator 31. The centrifugal pump 15a comprises a housing 32 having an inlet and an outlet (recognizable in FIG. 1 by means of arrows).

The centrifugal pump 15a is flowed through in the flow direction shown. The actuation of the impeller 25 is performed by means of a circumferential electromagnetic field generated by controlling the coils 29 of the stator 31.

Impeller magnets or at least ferromagnetic materials can be integrated into the impeller 25.

The support of the impeller 25 can then, on the one hand, be carried out by means of the impeller magnets and, on the other hand, by means of magnets provided outside the centrifugal pump. The magnets can be arranged circumferentially in the same movement of rotation as the impeller 25. Instead of the circumferential magnets or in addition hereto, also a circumferential electromagnetic field in a coil arrangement can support impeller 25 or fixate the said impeller 25 in a stable circumferential position, respectively. Though not shown in the figures, this embodiment is encompassed by the present invention as well.

Figure 8:
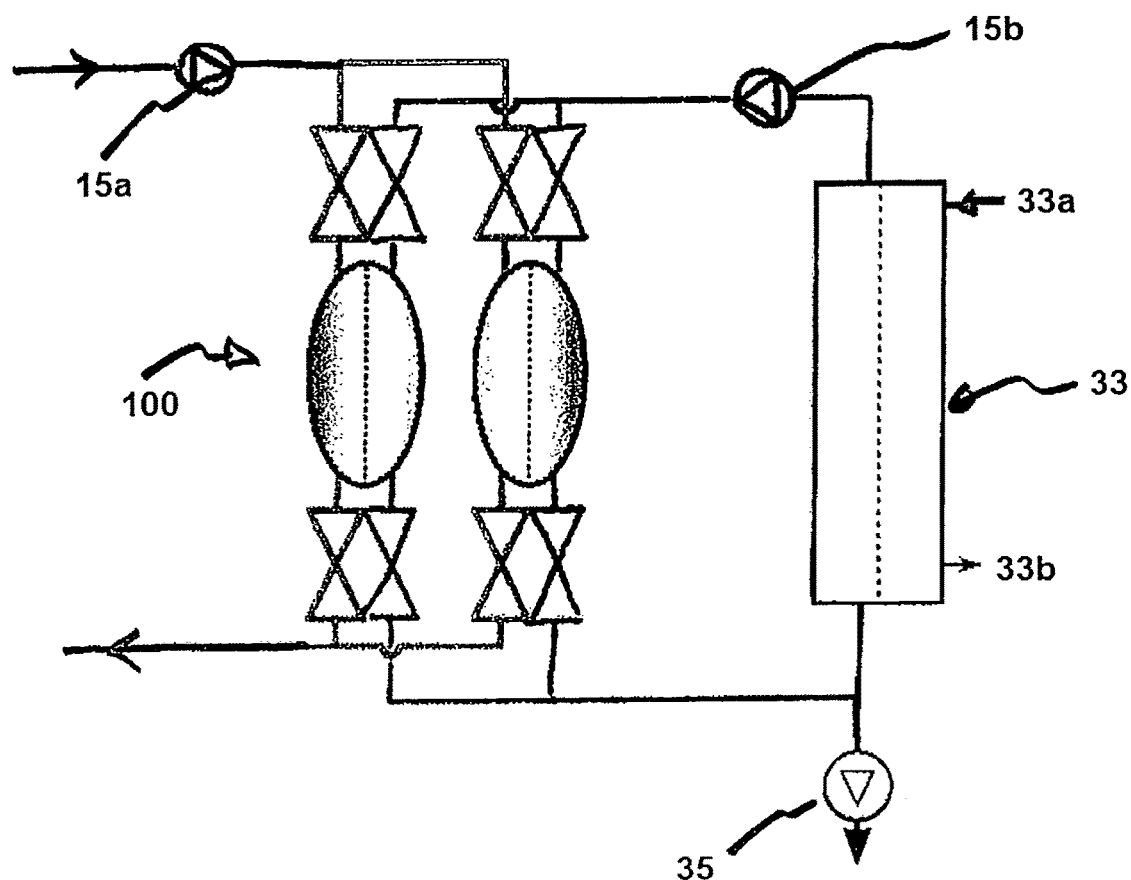
FIG. 8 shows an exemplary treatment apparatus according to the present invention comprising a balancing unit and an external medical functional unit in a schematically simplified manner.

FIG. 8 shows a balancing unit 100 according to the present invention and an exemplary treatment apparatus 300 according to the present invention comprising a dialyzer 33 comprising a blood inlet 33a and a blood outlet 33b as well as further elements or components, respectively, in a schematically simplified manner.

Figure 9:
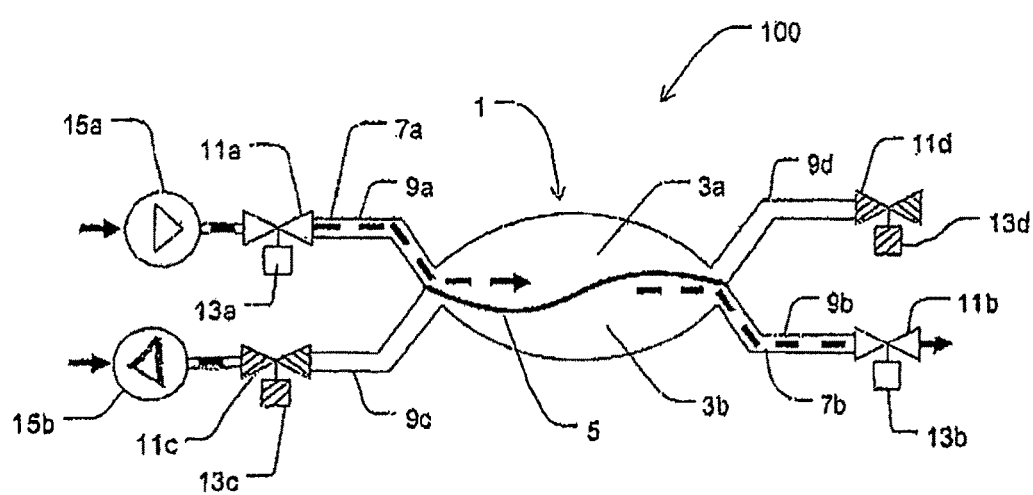
FIG. 9 shows an exemplary balancing unit according to the present invention in a further embodiment during a first cycle in a schematically simplified manner.

On the basis of FIG. 1, FIG. 9 shows an exemplary balancing unit according to the present invention of a further embodiment during a first cycle in a schematically simplified manner. It can be recognized that the centrifugal pump 15b conveys in a direction opposite to the direction of conveyance of the centrifugal pump 15a. By means of the conveying units pumping in directions opposite to each other of this embodiment, a too high initial pressure can advantageously be prevented or reduced. This can be the case when the dialysate is produced from RO water (reverse osmosis water) and concentrates. In doing so, the RO water supply can have such a high line pressure that the balancing unit could be damaged thereby.

The invention claimed is:

1. A balancing unit for medical fluids, the balancing unit comprising:
   a balancing chamber comprising a first compartment and a second compartment that are separated from each other by a fluid-tight membrane;
   a first conveying unit positioned along a first side of the balancing chamber, the first conveying unit configured to operate in a first direction toward the balancing chamber and to convey fluid in the first direction into the first compartment;
   a first valve positioned between the first conveying unit and the first compartment;
   a second conveying unit positioned along the first side or along a second side of the balancing chamber that is opposite to the first side, the second conveying unit configured to operate in a second direction opposite to the first direction and to convey fluid in the first direction past the second conveying unit and out of the second compartment while the second conveying unit operates in the second direction;
   a second valve positioned along the second side of the balancing chamber and adjacent the second compartment;
   a first control unit programmed to open the first valve during a first cycle in which the second valve is closed to allow fluid to flow in the first direction from the first conveying unit into the first compartment; and
   a second control unit programmed to open the second valve during a second cycle in which the first valve is closed to allow fluid to flow in the first direction and out of the second compartment;
   wherein each of the first and second conveying units is a centrifugal pump configured to control a filling pressure in the balancing chamber.

2. The balancing unit according to claim 1, wherein at least one of the first conveying unit and the second conveying unit comprises at least one rotational section supported magnetically.

3. The balancing unit according to claim 1, wherein at least one of the first conveying unit and the second conveying unit comprises at least one rotational section provided and designed for being actuated magnetically by an electromagnetic field.

4. An external medical functional unit comprising at least one balancing unit according to claim 1.

5. The external medical functional unit according to claim 4, wherein the external medical functional unit is configured as an external or extracorporeal blood circuit or blood cassette.

6. The external medical functional unit according to claim 4, configured as a disposable or single use article for insertion in a blood treatment apparatus.

7. A treatment apparatus for treating medical fluids, wherein the treatment apparatus is at least one of: (a) configured for operating at least one balancing unit according to claim 1, and (b) comprising at least one balancing unit according to claim 1.

8. The treatment apparatus according to claim 7, comprising an actuator provided and configured for actuating at least one of the first conveying unit and the second conveying unit of the balancing unit via a magnetic actuation interface.

9. The treatment apparatus according to claim 7, functionally connected with at least one of:
   the balancing unit, and an external medical functional unit comprising the balancing unit.

10. The treatment apparatus according to claim 7, configured as at least one of: a blood treatment apparatus and a hemodialysis machine.

11. A method for balancing a medical fluid using a balancing chamber that comprises first and second compartments that are separated from each other by a fluid-tight membrane, the method comprising the steps of:
   operating a first conveying unit positioned along a first side of the balancing chamber in a first direction toward the balancing chamber to convey the medical fluid in the first direction into the first compartment;
   controlling a first valve positioned between the first conveying unit and the first compartment to open during a first cycle to allow the medical fluid to flow in the first direction from the first conveying unit into the first compartment;
   operating a second conveying unit positioned along the first side or along a second side of the balancing chamber that is opposite to the first side in a second direction opposite to the first direction in a manner such that fluid is conveyed in the first direction past the second conveying unit and out of the second compartment; and
   controlling a second valve positioned along the second side of the balancing chamber and adjacent the second compartment to open during a second cycle to allow the medical fluid to flow in the first direction and out of the second compartment;
   wherein each of the first and second conveying units is a centrifugal pump configured to control a filling pressure in the balancing chamber.

12. The method according to claim 11, further comprising the step of: setting a maximum filling pressure of the balancing chamber.

13. The balancing unit according to claim 1, wherein the first conveying unit is positioned along the first side of the balancing chamber at which fluid can flow into the first compartment, such that the first conveying unit is located upstream of the balancing chamber.

14. The balancing unit according to claim 13, wherein the second conveying unit is positioned along the second side of the balancing chamber in a manner such that the second conveying unit is arranged to receive fluid flowing out of the second compartment, such that the second conveying unit is located downstream of the balancing chamber.

15. The balancing unit according to claim 13, wherein the second conveying unit is positioned along the first side of the balancing chamber at which fluid can flow into the second compartment, such that the second conveying unit is located upstream of the balancing chamber.

16. The balancing unit according to claim 1, wherein the first and second conveying units are configured to operate as constant pressure sources.

17. The external medical functional unit according to claim 5, wherein the second conveying unit acts as a pressure reducer to a portion of the external or extracorporeal blood circuit or blood cassette positioned downstream of the second conveying unit.

18. The method according to claim 11, wherein the first conveying unit is positioned along the first side of the balancing chamber at which fluid can flow into the first compartment, such that the first conveying unit is located upstream of the balancing chamber.

19. The method according to claim 18, wherein the second conveying unit is arranged to receive fluid flowing out of the second compartment, such that the second conveying unit is located downstream of the balancing chamber.

20. The method according to claim 18, wherein the second conveying unit is positioned along the first side of the balancing chamber at which fluid can flow into the second compartment, such that the second conveying unit is located upstream of the balancing chamber.

21. The method according to claim 11, further comprising operating the first and second conveying units as constant pressure sources.

22. The method according to claim 11, further comprising operating the second conveying unit to reduce a pressure in a portion of an external or extracorporeal blood circuit or blood cassette positioned downstream of the second conveying unit.

\* \* \* \* \*